(12) United States Patent
Minamoto et al.

(10) Patent No.: US 11,643,382 B2
(45) Date of Patent: May 9, 2023

(54) METHOD FOR PRODUCING 1-ACYLOXY-2-METHYL-2-PROPENE

(71) Applicant: KURARAY CO., LTD., Okayama (JP)

(72) Inventors: Naoya Minamoto, Ibaraki (JP); Yusuke Murata, Ibaraki (JP)

(73) Assignee: KURARAY CO., LTD., Okayama (JP)

( * ) Notice: Subject to any disclaimer, the term of this patent is extended or adjusted under 35 U.S.C. 154(b) by 0 days.

(21) Appl. No.: 17/259,613

(22) PCT Filed: Jul. 24, 2019

(86) PCT No.: PCT/JP2019/028951
§ 371 (c)(1),
(2) Date: Jan. 12, 2021

(87) PCT Pub. No.: WO2020/022365
PCT Pub. Date: Jan. 30, 2020

(65) Prior Publication Data
US 2021/0292268 A1    Sep. 23, 2021

(30) Foreign Application Priority Data
Jul. 27, 2018   (JP) .............................. JP2018-141808

(51) Int. Cl.
*C07C 67/055*   (2006.01)

(52) U.S. Cl.
CPC .................................. *C07C 67/055* (2013.01)

(58) Field of Classification Search
CPC .............................. C07C 67/055; C07C 69/145
See application file for complete search history.

(56) References Cited

U.S. PATENT DOCUMENTS 3,650,983 A * 3/1972 Miller ....................... B01J 23/96
                                                502/25
4,602,103 A    7/1986 Lyons

FOREIGN PATENT DOCUMENTS

| JP | S48-29712 A | | 4/1973 |
| JP | 084516 | * | 7/1975 |
| JP | S50-126612 A | | 10/1975 |
| JP | S52-27710 A | | 3/1977 |
| JP | S53-90212 A | | 8/1978 |
| JP | S53-127409 A | | 11/1978 |
| JP | S57-131741 A | | 8/1982 |
| JP | 2004-256459 A | | 9/2004 |
| JP | 256459 | * | 9/2004 |
| JP | 2005-320329 A | | 11/2005 |
| JP | 4710612 B2 | | 6/2011 |
| JP | 2016-50241 A | | 4/2016 |

OTHER PUBLICATIONS

JP 084516 translated (Year: 1975).*
JP 256459 translated (Year: 2004).*
ISR for PCT/JP2019/028951, dated Oct. 8, 2019.
EESR issued in EP Patent Application No. 19840405.5. Mar. 23, 2022.

* cited by examiner

*Primary Examiner* — Jafar F Parsa
*Assistant Examiner* — Blaine G Doletski
(74) *Attorney, Agent, or Firm* — Greenblum & Bernstein, P.L.C.

(57) ABSTRACT

A method for producing a 1-acyloxy-2-methyl-2-propene represented by the following general formula (II), including reacting a carboxylic acid represented by the following general formula (I), isobutylene, and oxygen, in the presence of a catalyst, in a liquid phase, with an amount of the isobutylene used of more than 1 mol and 50 mol or less per 1 mol of the carboxylic acid.

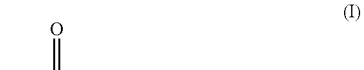

(I)

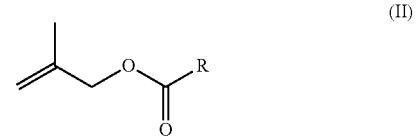

(II)

4 Claims, No Drawings

METHOD FOR PRODUCING 1-ACYLOXY-2-METHYL-2-PROPENE

TECHNICAL FIELD

The present invention relates to a method for producing a 1-acyloxy-2-methyl-2-propene.

BACKGROUND ART

A 1-acyloxy-2-methyl-2-propene has in one molecule thereof a 2,2-substituted carbon-carbon unsaturated bond applicable to radical addition reaction, hydrosilylation reaction, hydroformylation reaction, and the like, and an acyl group applicable to saponification reaction, ester exchange reaction, and the like, and thereby can be used as a production raw material of various chemical products due to the reactivity thereof (see, for example, PTL 1).

Some production methods of a 1-acyloxy-2-methyl-2-propene have been known.

For example, PTL 2 describes a method for producing 2-methyl-2-propenyl acetate (which may be hereinafter referred to as "methallyl acetate") through reaction of methallyl chloride and sodium acetate.

However, the production method generates an inorganic by-product, which generally becomes a waste material, in the equimolar amount or more with respect to the product. Accordingly, a production method that does not generate an inorganic by-product is demanded from the standpoint of the reduction of environmental load.

As a production method that does not generate an inorganic by-product, a method for producing a 1-acyloxy-2-methyl-2-propene through reaction of isobutylene, a carboxylic acid, and oxygen in a gas phase in the presence of a solid catalyst has been known.

For example, PTL 3 describes a method for producing methallyl acetate through reaction of isobutylene, acetic acid, and oxygen in a gas phase in the presence of the particular catalyst. PTL 3 describes that 870 g per hour of acetic acid, 850 NL per hour of isobutylene, and 75 NL of oxygen (isobutylene/acetic acid/oxygen=68/26/6 (molar ratio)) are fed to 1 L of the solid catalyst at 5 atm to perform gas phase reaction at a reaction temperature of 180° C., and thereby methallyl acetate is obtained with a selectivity of 96% in an amount of 270 g per hour. The conversion of isobutylene is 6.2%.

PTL 4 describes a method for producing methallyl acetate through reaction by feeding a mixed gas containing isobutylene, acetic acid, and oxygen to a palladium catalyst in a gas phase. PTL 4 describes that a mixed gas of isobutylene/acetic acid/oxygen/nitrogen=30/30/8/32 is fed at a rate of 10 L per hour to 10 mL of the solid catalyst to perform gas phase reaction at a reaction temperature of 160° C., and thereby methallyl acetate is obtained with a selectivity of 88% in a production efficiency of 538 mmol/(L(catalyst)·hr). The conversion of isobutylene is 4.7%.

A method for producing an unsaturated ester through reaction of a terminal olefin compound, a carboxylic acid, and oxygen in a liquid phase in the presence of a solid catalyst has been known.

For example, PTL 5 describes a method for producing methallyl acetate through reaction of isobutylene, acetic acid, and oxygen in the presence of a solid catalyst. PTL 5 describes that 10.0 g of acetic acid, 1.00 g of a hydrocarbon mixture containing 30% of isobutylene (molar ratio of isobutylene and acetic acid=1/31), and oxygen gas are subjected to liquid phase reaction at a reaction temperature of 85° C. in the presence of 1.00 g of a solid catalyst, and thereby methallyl acetate is obtained with a selectivity of 92% and a conversion of isobutylene of 71%.

CITATION LIST

Patent Literatures

PTL 1: JP 2016-50241 A
PTL 2: JP 2005-320329 A
PTL 3: JP 47-10612 A
PTL 4: JP 57-131741 A
PTL 5: JP 53-127409 A

SUMMARY OF INVENTION

Technical Problem

The reaction under the gas phase condition in PTLs 3 and 4 does not generate an inorganic by-product, but the oxygen concentration is necessarily the critical oxygen concentration or lower from the standpoint of safety, which constrains an operation with a low substrate conversion, requiring a recovery device for the substrate. Furthermore, the reaction requires a vaporizer of the raw materials, a reaction tube filled with the catalyst, and an enormous amount of energy for vaporizing the raw materials, and therefore there is large room for improvement in all the standpoints of the production efficiency, the equipment cost, and the energy consumption.

The production method of a 1-acyloxy-2-methyl-2-propene under the liquid phase condition in PTL 5 does not generate an inorganic by-product, does not require a vaporizer of the raw materials and a reaction tube filled with the catalyst, and does not require vaporization of the raw materials, and therefore the production method is advantageous from all the standpoints of the equipment cost and the energy consumption.

However, the aforementioned result specifically described in PTL 5 is in the case using a hydrocarbon mixture containing a large amount of other unsaturated compounds along with isobutylene as the substrate, and as a result of the reaction performed by the present inventors by using isobutylene as the substrate under the condition with an excess amount of acetic acid over isobutylene as similar to PTL 5, it has been found that the overreaction preferentially proceeds with the progress of the reaction, and the production efficiency of methallyl acetate cannot be increased.

In view of the circumstances, a problem to be solved by the present invention is to provide a method for producing a 1-acyloxy-2-methyl-2-propene that does not generate an inorganic by-product in the equimolar amount or more with respect to the product and is improved in production efficiency and cost.

Solution to Problem

As a result of the earnest investigations for solving the problem, the present inventors have found that the problem can be solved by producing a 1-acyloxy-2-methyl-2-propene under a particular liquid phase condition having an amount of isobutylene used of more than 1 mol and 50 mol or less per 1 mol of the carboxylic acid (I) described later, and the present invention has been completed by performing further investigations based on the knowledge.

Specifically, the present invention is as follows.

[1] A method for producing a 1-acyloxy-2-methyl-2-propene represented by the following general formula (II), including reacting a carboxylic acid represented by the following general formula (I), isobutylene, and oxygen, in the presence of a catalyst, in a liquid phase, with an amount of the isobutylene used of more than 1 mol and 50 mol or less per 1 mol of the carboxylic acid:

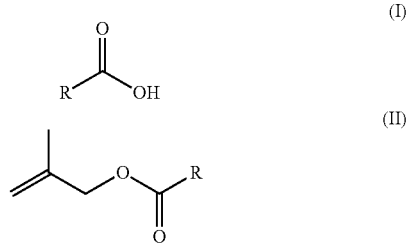

wherein R represents a hydrogen atom, an alkyl group having 1 to 8 carbon atoms, which may have a substituent, a cycloalkyl group having 3 to 8 carbon atoms, which may have a substituent, an alkenyl group having 2 to 6 carbon atoms, which may have a substituent, or an aryl group having 6 to 14 carbon atoms, which may have a substituent.

[2] The production method according to the item [1], wherein the carboxylic acid is acetic acid, and the 1-acyloxy-2-methyl-2-propene is 2-methyl-2-propenyl acetate.

[3] The production method according to the item [1] or [2], wherein the catalyst is a catalyst having carried thereon at least one kind of a noble metal.

[4] The production method according to any one of the items [1] to [3], wherein the catalyst is a catalyst containing palladium and at least one kind selected from transition metals of Group 8 to Group 11 in the periodic table.

[5] The production method according to any one of the items [1] to [4], wherein an amount of the catalyst used is from 0.01 to 20% by mass based on the total mass of the carboxylic acid and the isobutylene.

[6] The production method according to any one of the items [1] to [5], wherein a reaction temperature in the reaction in a liquid phase is from 80 to 200° C.

Advantageous Effects of Invention

According to the present invention, a method for producing a 1-acyloxy-2-methyl-2-propene that does not generate an inorganic by-product in the equimolar amount or more with respect to the product and is improved in production efficiency and cost can be provided.

DESCRIPTION OF EMBODIMENTS

The present invention will be described in detail below.

While preferred embodiments of the present invention will be described along with the matters defining the present invention, an embodiment combining two or more of the individual preferred embodiments is also a preferred embodiment of the present invention. In the case where there are plural numeral ranges for the matter shown by a numeral range, a combination of the lower limit and the upper limit that are selected from the plural ranges may also be a preferred embodiment.

The method for producing the 1-acyloxy-2-methyl-2-propene represented by the general formula (II) (which may be hereinafter abbreviated as a "1-acyloxy-2-methyl-2-propene (II)") of the present invention includes reacting the carboxylic acid represented by the general formula (I) (which may be hereinafter abbreviated as a "carboxylic acid (I)"), isobutylene, and oxygen, in the presence of a catalyst, in a liquid phase.

In the reaction, formally, isobutylene is oxidized and undergoes dehydration condensation with the carboxylic acid (I), so as to form the 1-acyloxy-2-methyl-2-propene (II) and water.

The reaction formula in a preferred embodiment of the present invention is as follows.

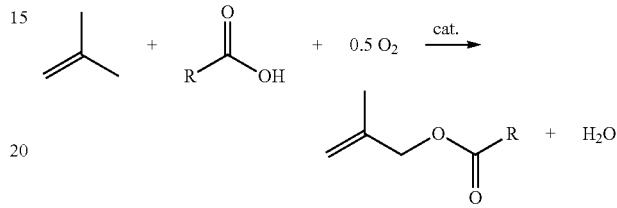

In the formula, R has the same meaning as R in the general formulae (I) and (II).

The overreaction that is not desired in the present invention is as follows.

Specifically, the produced 1-acyloxy-2-methyl-2-propene (II) is further oxidized and undergoes dehydration condensation with the carboxylic acid (I), so as to form a 1,3-bisacyloxy-2-methylenepropane and water.

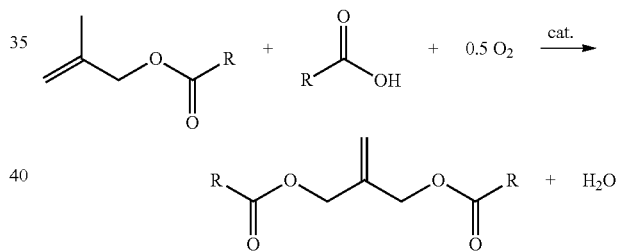

In the formula, R has the same meaning as R in the general formulae (I) and (II).

In the production method of the present invention, the costs of energy and equipment can be suppressed by employing the reaction under a liquid phase condition.

As a result of the investigations by the present inventors, it has been found that in a gas phase condition, a bisacyloxylated exomethylene compound as a major by-product is adsorbed on the catalyst and inhibits the reaction due to the high boiling point thereof. Accordingly, it is difficult to enhance the productivity in a gas phase condition, and a liquid phase condition is advantageous from the standpoint of the production efficiency.

As a result of the investigations by the present inventors, furthermore, it has been found that under the condition where the amount of isobutylene used is more than 1 mol and 50 mol or less per 1 mol of the carboxylic acid (I), the overreaction can be suppressed to provide the 1-acyloxy-2-methyl-2-propene (II) with a high production efficiency even though the substrate is reacted to a high conversion.

(Raw Materials and Target Product)

In the general formula (I) representing the carboxylic acid as the raw material and the general formula (II) representing the 1-acyloxy-2-methyl-2-propene as the target product, R represents a hydrogen atom, an alkyl group having 1 to 8 carbon atoms, which may have a substituent, a cycloalkyl group having 3 to 8 carbon atoms, which may have a substituent, an alkenyl group having 2 to 6 carbon atoms, which may have a substituent, or an aryl group having 6 to 14 carbon atoms, which may have a substituent.

The alkyl group having 1 to 8 carbon atoms represented by R may be linear or branched, and examples thereof include a methyl group, an ethyl group, a n-propyl group, an isopropyl group, a n-butyl group, a sec-butyl group, an isobutyl group, a tert-butyl group, a n-pentyl group, a n-hexyl group, and a n-octyl group.

In the alkyl group having 1 to 8 carbon atoms represented by R, one or more hydrogen atom may be substituted by a substituent. Examples of the substituent include a cycloalkyl group having 3 to 8 carbon atoms, an aryl group having 6 to 14 carbon atoms, an alkoxy group having 1 to 8 carbon atoms, an aryloxy group having 6 to 14 carbon atoms, and a silyl group. In the case where the alkyl group having 1 to 8 carbon atoms represented by R has a substituent, the number of the substituent is preferably 1 to 3. In the case where the alkyl group having 1 to 8 carbon atoms represented by R has plural substituents, the substituents may be the same as or different from each other.

Examples of the cycloalkyl group having 3 to 8 carbon atoms as the substituent include the same ones as exemplified for the cycloalkyl group having 3 to 8 carbon atoms represented by R described later.

Examples of the aryl group having 6 to 14 carbon atoms as the substituent include the same ones as exemplified for the aryl group having 6 to 14 carbon atoms represented by R described later.

Examples of the alkoxy group having 1 to 8 carbon atoms as the substituent include linear, branched, and cyclic alkoxy groups, such as a methoxy group, an ethoxy group, a propoxy group, a t-butoxy group, a pentyloxy group, a cyclopentyloxy group, a hexyloxy group, a cyclohexyloxy group, a 2-ethylhexyloxy group, and an octyloxy group.

Examples of the aryloxy group having 6 to 14 carbon atoms as the substituent include a phenoxy group and a naphthoxy group.

Examples of the silyl group as the substituent include a trimethylsilyl group, a triethylsilyl group, a t-butyldimethylsilyl group, a t-butyldiphenylsilyl group, and a triphenylsilyl group.

The cycloalkyl group having 3 to 8 carbon atoms represented by R may be any of monocyclic, polycyclic, and condensed ring, and examples thereof include a cyclopropyl group, a cyclopentyl group, and a cyclohexyl group.

In the cycloalkyl group having 3 to 8 carbon atoms represented by R, one or more hydrogen atom may be substituted by a substituent. Examples of the substituent include an alkyl group having 1 to 8 carbon atoms that is the same as the examples of the alkyl group having 1 to 8 carbon atoms represented by R described above, a cycloalkyl group having 3 to 8 carbon atoms that is the same as the examples of the cycloalkyl group having 3 to 8 carbon atoms represented by R described above, and an aryl group having 6 to 14 carbon atoms, an alkoxy group having 1 to 8 carbon atoms, an aryloxy group having 6 to 14 carbon atoms, and a silyl group that are the same as the examples of the substituent described above. In the case where the cycloalkyl group having 3 to 8 carbon atoms represented by R has a substituent, the number of the substituent is preferably 1 to 3. In the case where the cycloalkyl group having 3 to 8 carbon atoms represented by R has plural substituents, the substituents may be the same as or different from each other.

Examples of the alkenyl group having 2 to 6 carbon atoms represented by R include an ethenyl group (vinyl group), a 1-methylethenyl group, a 1-propenyl group, a 2-propenyl group (allyl group), a 1-methyl-1-propenyl group, a 1-methyl-2-propenyl group, a 1-butenyl group, a 2-butenyl group, and a 3-butenyl group.

In the alkenyl group having 2 to 6 carbon atoms represented by R, one or more hydrogen atom may be substituted by a substituent. Examples of the substituent include the same ones as exemplified for the substituent that may be had in the case where R represents an alkyl group having 1 to 8 carbon atoms. In the case where the alkenyl group having 2 to 6 carbon atoms represented by R has a substituent, the number of the substituent is preferably 1 to 3. In the case where the alkenyl group having 2 to 6 carbon atoms represented by R has plural substituents, the substituents may be the same as or different from each other.

The aryl group having 6 to 14 carbon atoms represented by R may be any of monocyclic, polycyclic, and condensed ring, and examples thereof include a phenyl group, a naphthyl group, an anthryl group, and a phenanthryl group.

In the aryl group having 6 to 14 carbon atoms represented by R, one or more hydrogen atom may be substituted by a substituent. Examples of the substituent include the same ones as exemplified for the substituent that may be had in the case where R represents a cycloalkyl group having 3 to 8 carbon atoms. In the case where the aryl group having 6 to 14 carbon atoms represented by R has a substituent, the number of the substituent is preferably 1 to 3. In the case where the aryl group having 6 to 14 carbon atoms represented by R has plural substituents, the substituents may be the same as or different from each other.

From the standpoint of the availability, R preferably represents an alkyl group having 1 to 8 carbon atoms or an alkenyl group having 2 to 6 carbon atoms, more preferably one selected from the group consisting of a methyl group, an ethyl group, a n-propyl group, a 2-propyl group, a n-butyl group, 2-butyl group, an isobutyl group, an ethenyl group, and a 1-methylethenyl group, further preferably a methyl group, a 2-propyl group, or a 1-methylethenyl group, and most preferably a methyl group or a 2-propyl group.

Accordingly, the carboxylic acid (I) is most preferably acetic acid or 2-methylpropanoic acid (isobutyric acid), and the 1-acyloxy-2-methyl-2-propene (II) is most preferably 2-methyl-2-propenyl acetate (methallyl acetate) or 2-methyl-2-propenyl isobutyrate (methallyl isobutyrate). In particular, the carboxylic acid (I) is preferably acetic acid, and the 1-acyloxy-2-methyl-2-propene is preferably 2-methyl-2-propenyl acetate (methallyl acetate).

(Catalyst)

It suffices that the catalyst used in the production method of the present invention is a catalyst that promotes the reaction of the carboxylic acid (I) and isobutylene, and a catalyst containing a carrier having a noble metal carried thereon is preferred. The catalyst may be a commercially available product and may be synthesized by a known method.

Carrier

The carrier used may be, for example, a porous substance. Examples of the carrier include an inorganic carrier, such as silica, alumina, silica-alumina, diatom earth, montmorillonite, zeolite, titania, zirconia, and activated carbon; and a polymer compound, such as polystyrene, polyethylene, polyamide, and cellulose. These may be used alone or as a combination of two or more kinds thereof. Among these, an inorganic carrier is preferred, silica or alumina is more preferred, and silica is further preferred. Silica may contain impurities other than $SiO_2$.

The form of the carrier is not particularly limited, and may be appropriately selected depending on the reaction mode. Specific examples of the form thereof include a powder form, a spherical form, and a pellet form, and a spherical form is preferred. In the case where the carrier has a spherical form, the particle diameter is not particularly limited, and is preferably 1 to 10 mm. In the case where the particle diameter is 10 mm or less, the raw materials can readily penetrate sufficiently into the interior of the catalyst, and the reaction can readily proceed effectively. In the case where the particle diameter is 1 mm or more, the carrier can readily exhibit the function thereof sufficiently Noble Metal Examples of the noble metal include palladium, gold, silver, platinum, rhodium, and ruthenium. These may be used alone or as a combination of two or more kinds thereof. Among these, palladium is preferred. Palladium herein may be in the form of metallic palladium or a palladium compound. The palladium compound is not particularly limited, and examples thereof include palladium chloride, palladium acetate, palladium nitrate, palladium sulfate, sodium chloropalladate, potassium chloropalladate, and barium chloropalladate.

In the case where the catalyst used contains a carrier having palladium carried thereon, the carrier may further carry, in addition to palladium, an element other than palladium, for example, a transition metal of Group 8 to Group 11 in the periodic table, such as iron, rhodium, copper, and gold; a base metal of Group 12 to Group 15 in the periodic table, such as zinc, indium, tin, and bismuth; or a metalloid of Group 13 to Group 16 in the periodic table, such as arsenic and tellurium. These may be used alone or as a combination of two or more kinds thereof. Among these, a transition metal of Group 8 to Group 11 in the periodic table is preferred, a transition metal of Group 11 in the periodic table is more preferred, and gold is further preferred, from the standpoint of the conversion and the selectivity of the reaction. The use form of the element other than palladium in the preparation of the catalyst is not particularly limited, and examples of the form include compound forms, such as a nitrate salt, a carbonate salt, a sulfate salt, an organic acid salt, and a halide.

In the case where the catalyst used contains a carrier having palladium and at least one kind selected from transition metals of Group 8 to Group 11 in the periodic table carried thereon, the ratio of palladium and the transition metal of Group 8 to Group 11 in the periodic table is preferably 0.001 to 10 parts by mass, and more preferably 0.05 to 5 parts by mass, of the transition metal of Group 8 to Group 11 in the periodic table per 1 part by mass of palladium.

The preparation method of the catalyst containing a carrier having palladium and a transition metal of Group 8 to Group 11 in the periodic table carried thereon is not particularly limited, and for example, the catalyst may be obtained by performing sequentially the following steps (1) to (4).

Step (1)
Step of impregnating a carrier with an aqueous solution of a palladium salt and a compound containing a transition metal of Group 8 to Group 11 in the periodic table, so as to provide a catalyst precursor A Step (2)
Step of bringing the catalyst precursor A obtained in the step (1) without drying, into contact with an aqueous solution of an alkali metal salt, so as to provide a catalyst precursor B Step (3)
Step of bringing the catalyst precursor B obtained in the step (2), into contact with a reducing agent, such as hydrazine or formalin, so as to provide a catalyst precursor C Step (4)
Step of rinsing with water and drying the catalyst precursor C obtained in the step (3)

The catalyst obtained by the aforementioned preparation method preferably has a specific surface area of 10 to 250 $m^2/g$ and a pore volume of 0.1 to 1.5 mL/g.

The ratio of the noble metal and the carrier in the catalyst is preferably 10 to 1,000 parts by mass, and more preferably 30 to 500 parts by mass, of the carrier per 1 part by mass of the noble metal. In the case where the amount of the carrier is 10 parts by mass or more per 1 part by mass of the noble metal, the dispersion state of the noble metal can be enhanced to improve the reaction result. In the case where the amount of the carrier is 1,000 parts by mass or less per 1 part by mass of the noble metal, the industrial practicality can be enhanced.

The amount of the catalyst used in the production method of the present invention is not particularly limited, and is preferably 0.01 to 20% by mass, more preferably 0.1 to 10% by mass, further preferably 1.0 to 10% by mass, and still further preferably 3.0 to 10% by mass, based on the total mass of the carboxylic acid (I) and isobutylene as 100% by mass.

(Oxygen)

Oxygen used in the production method of the present invention may be atomic and/or molecular oxygen, and is preferably molecular oxygen. In the case where molecular oxygen is used, a mixed gas with an inert gas, such as nitrogen, argon, helium, and carbon dioxide, is preferably used. In this case, it is more preferred that the oxygen concentration is controlled to such a range that the gas inside the system does not have an explosive composition.

Examples of the method of supplying molecular oxygen or a mixed gas containing molecular oxygen to the reaction system include a method of supplying to the liquid phase portion in the reaction system, a method of supplying to the gas phase portion therein, and a method of supplying to both the liquid phase portion and the gas phase portion.

Molecular oxygen or a mixed gas containing molecular oxygen is preferably supplied to the reaction system at an oxygen partial pressure in a range of 0.01 to 200 atm (gauge pressure), and more preferably 0.1 to 100 atm (gauge pressure).

(Catalyst Activator)

In the production method of the present invention, the reaction may be performed in the presence of a catalyst activator. The catalyst activator may be used in the form carried on the catalyst in advance, or may be charged in the reaction device along with the reaction mixture. Examples of the catalyst activator include a hydroxide, a nitrate salt, a carboxylate salt, or a carbonate salt of an alkali metal, such as sodium, potassium, and cesium; and a hydroxide, a nitrate salt, a carboxylate salt, or a carbonate salt of an alkaline earth metal, such as magnesium, calcium, and barium. These catalyst activators may be used alone or as a combination of two or more kinds thereof. Among these, a salt of the carboxylic acid (I) is preferred, an alkali metal salt of the carboxylic acid (I) is more preferred, and potassium acetate is further preferred, from the standpoint of the availability and the reaction activity.

The amount of the catalyst activator used is not particularly limited, and is preferably 1 to 20% by mass, and more preferably 3 to 15% by mass, based on the mass of the catalyst (which is the mass including the catalyst activator in the case where the catalyst activator is carried on the catalyst).

(Solvent)

The reaction of the carboxylic acid (I), isobutylene, and oxygen in the presence of a catalyst in a liquid phase in the production method of the present invention may be performed by using a solvent or without a solvent.

Examples of the solvent that is used depending on necessity in the production method of the present invention include a hydrocarbon (including an aliphatic hydrocarbon and an aromatic hydrocarbon), such as hexane, heptane, methylcyclohexane, and benzene; a heterocyclic compound, such as pyridine and quinoline; an ether, such as diethyl ether, tetrahydrofuran, methyl tert-butyl ether, and cyclopentyl methyl ether; a ketone, such as acetone, methyl ethyl ketone, and isobutyl methyl ketone; an ester, such as a carboxylate ester, diethyl carbonate, and propylene carbonate; an amide, such as dimethylformamide and dimethylacetamide; a nitrile, such as acetonitrile and benzonitrile; and an alcohol, such as methanol, ethanol, isopropyl alcohol, and phenol. These may be used alone or as a combination of two or more kinds thereof.

In the case where a solvent is used in the reaction, the amount of the solvent used is not particularly limited, as far as the reaction is not adversely affected, and is generally approximately 0.1 to 1,000 times amount, and is preferably 0.4 to 100 times amount from the standpoint of the productivity, all based on the total mass of the carboxylic acid (I) and isobutylene.

(Reaction Condition)

In the production method of the present invention, the amount of the isobutylene used is more than 1 mol and 50 mol or less per 1 mol of the carboxylic acid (I). The amount of the isobutylene used (i.e., the amount thereof used per 1 mol of the carboxylic acid) is preferably 1.5 mol or more, and more preferably 2 mol or more, and may be 5 mol or more or 8 mol or more. The amount of the isobutylene used is preferably 45 mol or less, more preferably 40 mol or less, and further preferably 35 mol or less. In the case where the amount thereof used is 1 mol or less, the 1-acyloxy-2-methyl-2-propene (II) cannot be obtained with high production efficiency due to the progress of the overreaction. With the amount thereof used of more than 1 mol, excellent production efficiency can be obtained. In the case where the amount thereof used exceeds 50 mol, the process for recovering the excessive isobutylene is prolonged, which is not economically preferred.

In the case where the carboxylic acid (I) is placed in the reaction system by dividing into multiple times, the amount thereof used is the total amount thereof placed.

The reaction conditions, such as the reaction temperature, the reaction pressure, and the reaction time, in the production method of the present invention may be appropriately determined depending on the kinds and the combination of the carboxylic acid (I), isobutylene, and the solvent used depending on necessity, the composition of the catalyst, and the like, and are not particularly limited.

For example, the reaction temperature is preferably in a range of 80 to 200° C. In the case where the reaction temperature is 80° C. or more, the 1-acyloxy-2-methyl-2-propene (II) can be efficiently produced without excessive decrease of the reaction rate. The reaction temperature is more preferably 90° C. or more, and further preferably 120° C. of more. In the case where the reaction temperature is 200° C. or less, side reaction including combustion can be prevented from occurring, and thereby the 1-acyloxy-2-methyl-2-propene (II) can be efficiently produced, and the corrosion of the reaction device due to the carboxylic acid can be suppressed. The reaction temperature is more preferably 180° C. or less, and further preferably 160° C. or less.

The reaction time may be in a range, for example, of 0.5 to 12 hours. The reaction time may be 1 hour or more from the standpoint of the production efficiency, and may be 10 hours or less or 8 hours or less from the same standpoint.

The reaction mode in the production method of the present invention may be either a continuous system or a batch system, and is not particularly limited. In the case where a batch system is used as the reaction mode, for example, the catalyst may be charged in the reaction device at one time along with the raw materials, and in the case where a continuous system is used as the reaction mode, for example, the catalyst may be charged in the reaction device in advance, or may be continuously charged in the reaction device along with the raw materials. The catalyst may be used in the form of any of a fixed bed, a fluidized bed, and a suspension bed.

(Purification)

In the production method of the present invention, purification may be performed after the aforementioned reaction. Specifically, the 1-acyloxy-2-methyl-2-propene (II) formed through the aforementioned reaction can be isolated by separating the catalyst and then purifying the reaction solution.

The measure for separating the catalyst is not particularly limited and may be an ordinary solid-liquid separation measure, and examples thereof used include filtration methods, such as natural filtration, pressure filtration, filtration under reduced pressure, and centrifugal filtration.

The measure for purifying the reaction solution is not particularly limited and may be a distillation method, an extraction method, column chromatography, or the like. These methods may be performed in combination. Among these, a distillation method and an extraction method are preferred.

The raw materials and the solvent separated by the purification may be used again for the reaction. The catalyst separated may also be used again in the reaction.

The production method of the present invention exemplified by the aforementioned embodiments can produce the 1-acyloxy-2-methyl-2-propene (II) as the target product with a high conversion, a high selectivity, and a high yield, without the formation of the inorganic by-product in the equimolar amount or more with respect to the target product.

EXAMPLES

The present invention will be described more specifically with reference to examples and comparative examples below, but the present invention is not limited thereto.

[Analysis Condition]

The solution after the reaction (reaction mixture) was analyzed by using a gas chromatograph GC2014 (produced by Shimadzu Corporation, FID detector) and a capillary column (produced by Agilent Technologies, Inc., DB-1, length: 30 m, inner diameter: 0.25 mm, thickness: 0.25 μm) under the following condition.

Column temperature: 50° C. (5 min)→10° C./min→250° C. (5 min)
FID temperature: 250° C.
Injection port temperature: 250° C.
Carrier gas: helium
Makeup gas: helium
Injection amount: 0.2 μL
Gas flow rate in column: 0.38 mL/min
Split ratio: 20

Production Example: Preparation of Catalyst 250 mL of a silica carrier (5 mm in diameter) was immersed in an aqueous solution containing 4.00 g (13.6 mmol) of sodium tetrachloropalladate and 3.90 g (9.5 mmol) of tetrachloroauric acid tetrahydrate, and the entire amount of the aqueous solution was absorbed thereby. Subsequently, 200 mL of an aqueous solution containing 16 g (131 mmol) of sodium metasilicate was added thereto, and the mixture was allowed to stand for 20 hours. Thereafter, 9.50 g (190 mmol) of hydrazine monohydrate was added to reduce the palladium salt and the gold salt to metals. The catalyst after the reduction was rinsed with water and dried at 110° C. for 4 hours to prepare the catalyst.

Example 1

1.3 g of the catalyst obtained in Production Example, 2.4 g (41 mmol) of acetic acid, and 22.8 g (406 mmol) of isobutylene were charged in an electromagnetic stirring autoclave having a capacity of 100 mL equipped with a gas inlet port and a sampling port, a mixed gas of oxygen/nitrogen=8/92 (molar ratio) was introduced to the liquid phase to make the pressure inside the autoclave of 20 atm (gauge pressure), and then the temperature in the autoclave was increased to 140° C. under stirring. Thereafter, the reaction was performed for 5 hours while flowing a mixed gas of oxygen/nitrogen=8/92 (molar ratio) at a flow rate of 200 mL/min and retaining 90 atm (gauge pressure) with the mixed gas, so as to provide a reaction solution.

The analysis of the resulting reaction solution by the aforementioned method revealed that the conversion of acetic acid was 98%, and the selectivity to methallyl acetate was 90%. The yield of methallyl acetate obtained was 4.1 g (36 mmol), and the production efficiency of methallyl acetate was 0.64 g(product)/(g(catalyst)·hr).

Example 2

The reaction was performed by performing the same procedure as in Example 1 except that 0.84 g (14 mmol) of acetic acid and 23.5 g (419 mmol) of isobutylene were used.

The analysis of the resulting reaction solution by the aforementioned method revealed that the conversion of acetic acid was 98%, and the selectivity to methallyl acetate was 88%. The yield of methallyl acetate obtained was 1.4 g (12 mmol), and the production efficiency of methallyl acetate was 0.22 g(product)/(g(catalyst)·hr).

Example 3

The reaction was performed by performing the same procedure as in Example 1 except that 2.6 g of the catalyst and 3.6 g (41 mmol) of isobutyric acid instead of acetic acid were used.

The analysis of the resulting reaction solution by the aforementioned method revealed that the conversion of isobutyric acid was 77%, and the selectivity to methallyl isobutyrate was 87%. The yield of methallyl isobutyrate was 3.8 g (27 mmol), and the production efficiency of methallyl isobutyrate was 0.30 g(product)/(g(catalyst)·hr).

Comparative Example 1

The reaction was performed by performing the same procedure as in Example 1 except that 42.2 g (703 mmol) of acetic acid and 3.9 g (70 mmol) of isobutylene were used.

After the reaction for 5 hours, the conversion of isobutylene was 53%, and the selectivity to methallyl acetate was 74%. The reaction was further continued, and after 23 hours, the conversion of isobutylene was increased to 91%, but the overreaction of methallyl acetate to 1,3-diacetoxy-2-methylenepropane proceeded to decrease the selectivity to methallyl acetate to 45%.

After the reaction for 5 hours, the yield of methallyl acetate was 3.1 g (27.4 mmol), and the production efficiency of methallyl acetate was 0.49 g(product)/(g(catalyst)·hr), and after the reaction for 23 hours, the yield of methallyl acetate was 3.3 g (28.8 mmol), and the production efficiency of methallyl acetate was 0.11 g(product)/(g(catalyst)·hr).

Comparative Example 2

8.6 g (approximately 15 mL) of the catalyst obtained in Production Example was packed in a reaction tube formed of stainless steel having an inner diameter of 23 mm and a length of 20 cm, through which isobutylene, acetic acid, oxygen, nitrogen, and water were loaded at a volume ratio (in terms of gas) of isobutylene/acetic acid/oxygen/nitrogen/water=30/7/8/53/2 and a rate of 70.5 NL/hr, and reacted under pressure of 0.5 MPaG at 160° C. After 4 hours, the analysis of the composition in the outlet port of the reaction tube revealed that the production rate of methallyl acetate was 0.16 g(product)/(g(catalyst)·hr), and the yield of methallyl acetate with respect to acetic acid loaded to the reaction tube was 5.5%. Carbon dioxide was generated at a selectivity of 5.5% with respect to isobutylene reacted.

Thereafter, after loading only nitrogen at 160° C. under the atmospheric pressure at a rate of 70 NL/hr for 1 hour, the reaction tube was cooled to room temperature, and the catalyst was taken out therefrom. 1 g of the catalyst was immersed in 10 mL of methanol, and the analysis of the solution confirmed the presence of 1,3-diacetoxy-2-methylenepropane. Accordingly, it was found that 1,3-diacetoxy-2-methylenepropane was not sufficiently vaporized but was adsorbed on the catalyst under the reaction condition.

The results of Examples 1 to 3 and Comparative Examples 1 and 2 shown above are shown in Table 1.

TABLE 1

|  | Reaction phase | Carboxylic acid (I) | Molar ratio [1] | Reaction time (hr) | Conversion | Selectivity [2] | Yield | Production efficiency [3] |
| --- | --- | --- | --- | --- | --- | --- | --- | --- |
| Example 1 | liquid phase | acetic acid | 10/1 | 5 | 98% [4] | 90% | 88% [4] | 0.64 |
| Example 2 | liquid phase | acetic acid | 30/1 | 5 | 98% [4] | 88% | 86% [4] | 0.22 |
| Example 3 | liquid phase | isobutyric acid | 10/1 | 5 | 77% [4] | 87% | 66% [4] | 0.30 |

TABLE 1-continued

| | Reaction phase | Carboxylic acid (I) | Molar ratio *1 | Reaction time (hr) | Conversion | Selectivity *2 | Yield | Production efficiency *3 |
|---|---|---|---|---|---|---|---|---|
| Comparative Example 1 | liquid phase | acetic acid | 1/10 | 5<br>23 | 53% *5<br>91% *5 | 74%<br>45% | 39% *5<br>41% *5 | 0.49<br>0.11 |
| Comparative Example 2 | gas phase | acetic acid | 30/7 | 4 | 14% *4 | 39% | 5.5% *4 | 0.16 |

The expressions in Table 1 are as follows.
*1: Isobutylene/carboxylic acid (I)
*2: Selectivity to 1-acyloxy-2-methyl-2-propene (II) in product
*3: Production efficiency of 1-acyloxy-2-methyl-2-propene (II) (g(product)/(g(catalyst)·hr))
*4: Based on carboxylic acid (I)
*5: Based on isobutylene Examples 1 to 3 each show an excellent selectivity, from which it is understood that an inorganic by-product is not formed in the equimolar amount or more with respect to the product. It is also understood from the conversion, the selectivity, and the yield that Examples are excellent in production efficiency as compared to Comparative Examples.

INDUSTRIAL APPLICABILITY

According to the production method of the present invention, a 1-acyloxy-2-methyl-2-propene can be produced without the generation of an inorganic by-product in the equimolar amount or more with high production efficiency and cost efficiency. A 1-acyloxy-2-methyl-2-propene can be used as a production raw material of various industrially useful compounds.

The invention claimed is:

1. A method for producing a 1-acyloxy-2-methyl-2-propene represented by the following general formula (II), comprising reacting
a carboxylic acid represented by the following general formula (I),
isobutylene, and
oxygen,
in the presence of a catalyst, in a liquid phase, with an amount of the isobutylene used of 8 mol or more and 50 mol or less per 1 mol of the carboxylic acid:

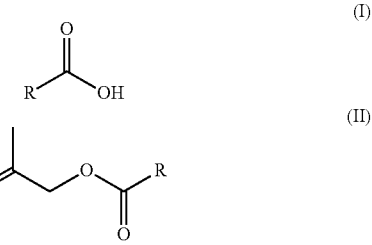

wherein R represents a hydrogen atom, an alkyl group having 1 to 8 carbon atoms, which may have a substituent, a cycloalkyl group having 3 to 8 carbon atoms, which may have a substituent, an alkenyl group having 2 to 6 carbon atoms, which may have a substituent, or an aryl group having 6 to 14 carbon atoms, which may have a substituent,
wherein the catalyst comprises a support carrying
palladium and
at least one selected from transition metals of Group 8 to Group 11 in the periodic table.

2. The production method according to claim 1, wherein the carboxylic acid is acetic acid, and
the 1-acyloxy-2-methyl-2-propene is 2-methyl-2-propenyl acetate.

3. The production method according to claim 1, wherein an amount of the catalyst used is from 0.01 to 20% by mass based on the total mass of the carboxylic acid and the isobutylene.

4. The production method according to claim 1, wherein a reaction temperature in the reaction in a liquid phase is from 80 to 200° C.

* * * * *